United States Patent [19]

Magat et al.

[11] 4,431,071
[45] Feb. 14, 1984

[54] APPARATUS FOR DETERMINING THE MASS BY THE HECTOLITRE (SPECIFIC WEIGHT) OF VARIOUS PRODUCTS SUCH AS FOODSTUFFS, MORE PARTICULARLY CEREALS, GRANULAR PRODUCTS AND THE LIKE

[76] Inventors: Georges Magat, 16 Rue du 8 Mai; Jean Magat, 8 Rue du 8 Mai, both of 42110 Feurs, France

[21] Appl. No.: 290,816

[22] Filed: Aug. 7, 1981

[30] Foreign Application Priority Data

Aug. 8, 1980 [FR] France ................................ 80 18081

[51] Int. Cl.³ ...................... G01G 19/56; G01G 23/02
[52] U.S. Cl. ..................................... 177/149; 177/156
[58] Field of Search ................. 177/59, 145, 148, 149, 177/154, 156, 25, 246

[56] References Cited

U.S. PATENT DOCUMENTS

| | | | |
|---|---|---|---|
| 500,045 | 6/1893 | Wood | 177/59 |
| 2,185,045 | 12/1939 | Unruh et al. | 177/154 |
| 2,408,906 | 10/1946 | Bocchicchio | 177/145 X |
| 2,689,082 | 9/1954 | Kolisch | 177/25 X |
| 2,708,368 | 5/1955 | Kolisch | 177/25 X |
| 3,741,326 | 6/1973 | Scraper | 177/59 |
| 4,308,928 | 1/1982 | Oshima | 177/59 X |
| 4,347,905 | 9/1982 | Berckes | 177/246 X |

Primary Examiner—George H. Miller, Jr.
Attorney, Agent, or Firm—Eric P. Schellin

[57] ABSTRACT

A device for determining the specific weight of granular products by weighing a fixed volume in a tapered hopper that can be locked in place, filled, unlocked to be weighed, and tipped over to dispense the granular products.

14 Claims, 12 Drawing Figures

APPARATUS FOR DETERMINING THE MASS BY THE HECTOLITRE (SPECIFIC WEIGHT) OF VARIOUS PRODUCTS SUCH AS FOODSTUFFS, MORE PARTICULARLY CEREALS, GRANULOUS PRODUCTS AND THE LIKE

In accordance with the prior art, the measurement of the mass by the hectoliter of cereals and other granulous products is performed as follows:

A tapering hopper, located above a measure established and standardized with respect to the characteristics thereof by the corresponding rules and specifications, is filled with the products. When the measure is filled and flush with the products, an operator removes it while placing it manually on a weighting machine for determining the weight of the contents. The latter is then, by a further handling, discharged into sacks or the like for another operation, and then the hopper is positioned again upon the empty measure for a further operational step.

It will be clearly understood that this weighing method has various disadvantages.

As an information, for some products such as corn and other cereals, and according to the specifications, the measure has a weight of 10 kilogrammes when empty, and of 50 kilogrammes when loaded. It will be obvious that this heavy load to be carried many times is surely straining for the operator. This method is unpractical, lengthy and tedious. Accordingly, it has been found that some operators proper had a tendency to appreciate in a subjective manner the weights of the loads after some actual measurements, with the obvious possibility of an error which is not negligible with respect to the actual specific weight, this error being repeated in accordance with the number of operations.

An object of the invention is an apparatus making it possible to determine automatically the mass by the hectoliter of the cereals and other granulous products, while reducing to a minimum the duties of the operator which consist in controlling and positioning some means permitting the operation of the automatic measurement.

A further object in accordance with the invention is to provide a novel method for weighing the cereals and other granulous products showing the direct indication of the mass by the hectoliter.

According to a first characteristic, the apparatus for measuring the mass by the hectoliter (specific weight) of foodstuffs, more particularly cereals, granulous products and the like, is characterized in that the apparatus includes a frame within which a receiving hopper and a measure of reference are positioned independently, a weighing machine disposed in the upper portion of the frame receiving on the scale thereof a clevis resting on said scale and said measure being supported at the lower portion of the clevis, said apparatus comprising moreover means for interlocking the clevis in some operational steps, and means permitting said measure to be tilted after the determination of the weight, the apparatus being arranged so that the weight of the products will be determined automatically without handling of the measure between the filling location thereof, the weighing location thereof and the emptying position thereof for discharging the products after the weighing.

In accordance with a further characteristic, the apparatus is characterized in that the frame is provided with means for interlocking in position the clevis and the supporting means for the tapering hopper.

According to a further object of the invention, the use of the apparatus has been developed by taking away the granulous products, cereals and the like, directly at the time of the tilting of the trap-door of a vehicle for pouring the products into the receiving pit.

In accordance with a further characteristic, the upper portion of the frame permits laterally or transversely the fastening of a clevis provided with an off-set hanging means and hinging means for the end of a feeder with a worm gear which is driven by a motor, the base of said feeder being provided with a roller for resting on the ground and permitting the feeder to be pivoted for 180 degrees with respect to said apparatus, in order to position the lower collector thereof opposite the downfall of the products, the upper portion of said feeder supporting a sleeve for free rotation within a hopper having an extension in the form of a bent chute for pouring down the products into the hopper proper of the apparatus.

The advantages of this application are pointed out:

the novel weighing method is simple, practical, and highly efficient;

the hopper is independent relative to the weighing device;

the handling by man power is entirely eliminated;

the fast and automatic treatment, taking place directly when the products are poured down from the trap-door of a vehicle.

These and other characteristics will be clearly apparent from the following description.

Figure 1:
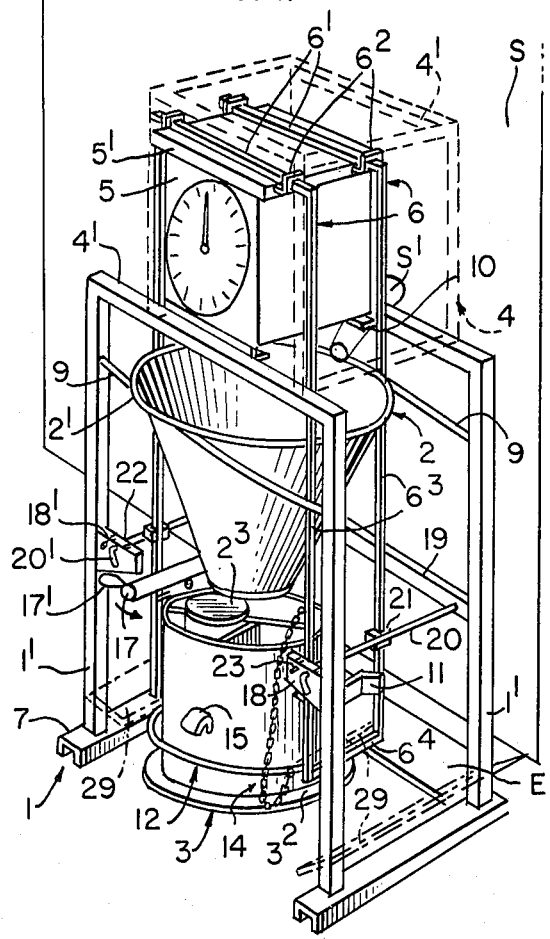
FIG. 1 is a perspective view of the apparatus, before filling the measure.
Figure 2:
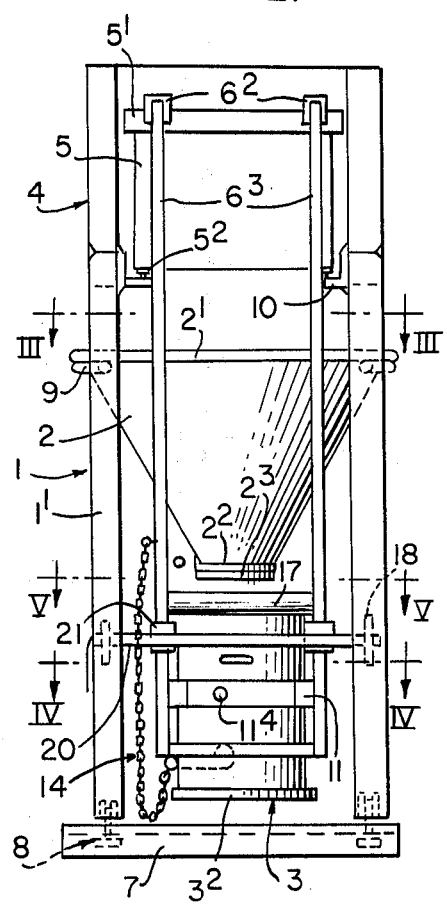
FIG. 2 is a side view according to FIG. 1.

The apparatus has been illustrated as a perspective view in FIG. 1. This apparatus includes five main elements, namely : a frame (1) within which a tapering hopper (2) and a measure (3) are positioned independently, a housing (4) of reduced size in superimposed abutment on the frame, a weighing machine (5) secured in abutment on the upper portion of the frame and protected by the housing, a clevis (6) in abutment on the scale ($5^1$) of the weighing machine and supporting at the lower portion thereof the measure (3) and the tapering hopper (2) disposed in a fixed manner on the frame (1). Other important means will be apparent hereinafter.

In accordance with a first characteristic, the frame is provided with means for supporting the tapering hopper and with means for interlocking the clevis in position. The frame (1) is comprised of vertical and horizontal posts of squared section, or made up for instance of U-shaped irons. The lower ends of the vertical posts ($1^1$) are made fast with U-shaped cross-pieces (7) by means of fastening elements. The frame is vertically adjustable by means of pressure cylinders (8). These vertical posts ($1^1$) are conveniently spaced and braced on the lateral sides and the bottom side of said frame (1). The hopper is supported in a final manner and independently the measure by two arches (9) having a curved outline for co-operating with the edge ($2^1$) of the hopper (2). These arches (9) are secured at the ends thereof to the posts ($1^1$) of the frame by welding or the like. The hopper has in the bottom ($2^2$) thereof an opening with a closure door ($2^3$).

At the upper portion of the frame (1), longitudinally or transversely to the bracing bars or tie-bars ($1^2$) are secured L-shaped angle irons (10) the dimensions of which are substantially larger than the dimensions of the weighing machine (5) the footing ($5^2$) of which is abutting on said angle irons.

In accordance with a further characteristic, a housing (4) the length of which is smaller than the length of the frame (1) is abutting on the latter and has the function to cover and to protect the weighing machine (5).

In accordance with a further characteristic, the upper portion of the clevis-shaped element (6) is disposed in abutment on the scale ($5^1$) of the weighing machine, and has more particularly the function to support the measure (3). For this purpose, this supporting element consists of two horizontal bars ($6^1$) abutting and centered by means of inserted small plates ($6^2$) on the scale of the weighing machine. Said small plates ($6^2$) are secured by welding or the like to the bars ($6^1$). These horizontal bars ($6^1$), at the ends thereof, are extended downwardly in the form of vertical bars ($6^3$), defining thereby a clevis. A portion of the vertical bars is substantially engaged within the profile of the bars ($4^1$) of the housing (4), while the lower portion has an extension downwardly while remaining substantially away from the edge ($2^1$) of the tapering hopper, in order to prevent any contact with the latter.

Figure 4:
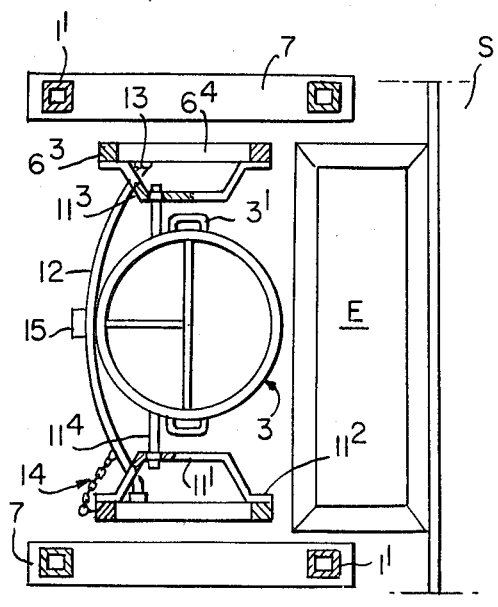
FIG. 4 is a cross-sectional view from above along the line IV-IV of FIG. 2, at the level of the articulation of the meaure.
Figure 3:
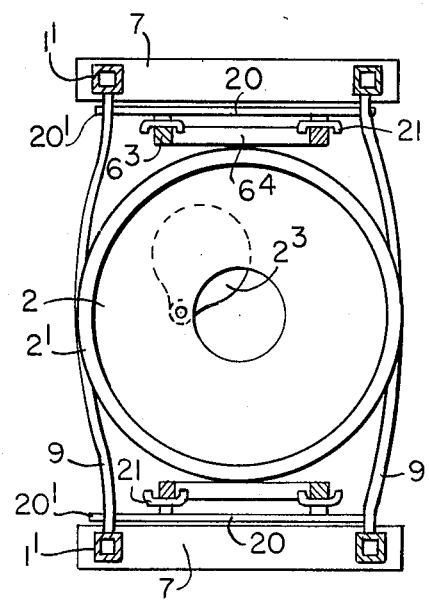
FIG. 3 is a view from above in vertical cross-section, along the line III—III of FIG. 2, underneath the hopper.

In accordance with a further characteristic, the profiled plates (11) are inserted and secured at each one of their ends to the bars ($6^3$) of the clevis (6). Each plate has an off-set central portion ($11^1$), while the webs ($11^2$) thereof are provided with openings for the passage of fastening screws or the like extending into said bars. Moreover, the central portion ($11^1$) is provided with an opening ($11^3$) for the engagement and the abutment of two pins ($11^4$) integral with the measure. These pins are mounted for free rotation within the aforesaid openings, permitting thereby the tilting of the measure, while their transverse shifting is prevented by convenient means. These pins ($11^4$) are inserted and welded against the gripping handles ($3^1$) of the measure (3). An important feature, as will be seen in FIG. 4 of the drawings, is that both pins are off-set relative to the medial transverse axis of said measure. Therefore, it will be clearly understood that it is necessary to provide an interlocking means in the vertical position of the measure, said means being retractable in order to permit the measure to be emptied. In a known manner, the measure has a peripheral edge ($3^2$) which defines, so to speak, the footing thereof. In accordance with the invention, there is provided a third (12) which is conveniently shaped and retractable under the action of the operator. For this purpose, said arch is in abutment by the central portion thereof against the measure, while the ends of the arch are established so that they will extend substantially along the lower cross-pieces ($6^4$) of the clevis. On each one of them is provided a second finger (13) on which the end ($12^1$) of the third arch (12) is engaged for free swivelling. A motion of translation of said ends is prevented by a convenient means. Moreover, there has been provided a small chain (14) the ends ($14^1$) of which are secured to the arch proper and to one of the vertical bars of the clevis, with some slack corresponding to the maximal lowering of the arch relative to the initial position thereof.

In accordance with a further characteristic, a handle or pedal (15) has been provided on the body of the measure, and is depressed by the operator in an operational step which is determined with accuracy in order to disengage the measure from the arch, while ensuring the interlocking of the measure in position. This pedal (15) is located somewhat at a higher level with respect to the bearing plane of the arch.

Figure 5:
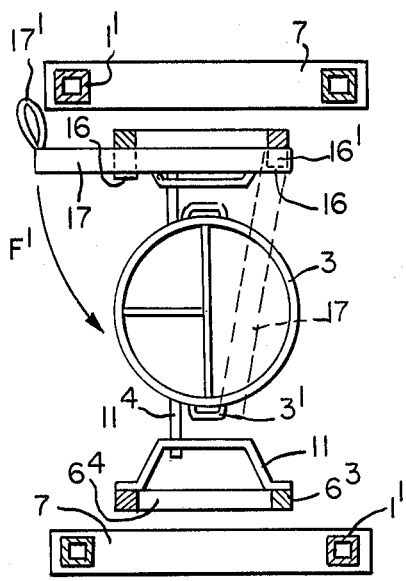
FIG. 5 is a cross-sectional view from above along the line V—V of FIG. 2, between the hopper and the measure.

In accordance with a further characteristic, which is more particularly illustrated in FIG. 1 and 5, two profiled lugs (16) for positioning a flushing roll (17) are provided on the bars of the measure-holding clevis, at the level of the upper plane of said bars. For this purpose, the lug (16) located on the rear bar of the clevis is provided with a second finger ($16^1$) for the engagement of the end of a lug which forms an extension of said roll, an interlocking means against a motion of translation being provided and inserted on the finger to prevent the undesired removal of the roll. In the inactive position, the latter is resting on said lugs, while when used, by gripping of the handle ($17^1$) thereof, the roll is pivoted and moved transversely around the rotational axis thereof, permitting thereby the measure to be filled flush.

In accordance with a further important characteristic of the invention, a device for interlocking and unlocking in position the measure-holding clevis is provided, so that the weighing machine will not be damaged and warped when the measure is loaded and emptied. For this purpose, profiled brackets (18) are disposed on the vertical posts ($1^1$) of the frame, and a bracing cross-bar (19), located at the same level as the brackets, is disposed between the rear posts. The latter have a cut out ($18^1$) in which a three pin (20) is abutted and engaged for free rotation in order to support the interlocking elements (21). This pin is engaged and fixed for free rotation within the cross-bar (19), means being provided for preventing the transverse shifting of said third pin (20).

Figure 6:
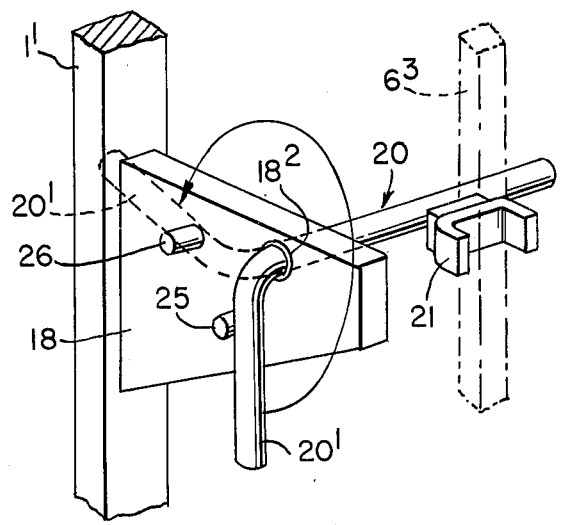
FIG. 6 is a perspective view on a larger scale, illustrating the interlocking and the unlocking of the suporting clevis for the measure.

In accordance with a first form of embodiment, the steady positioning of said pin within the location thereof is provided by an interlocking pawl (22). This third pin (20) has at the end thereof an extension in the form of a gripping handle (20¹). Moreover, an abutting finger (23) is provided on each one of the brackets, the handle of the third pin (20), after pivotal motion thereof, being abutted against this finger. Opposite the bars of the clevis which is facing said pin, the pin is provided with anchoring profiles (21) having a form which is complementary to the section of the bars, in order to maintain the latter in a steady position. These anchoring profiles can be in the form of tongs, of hooks; in an alternative form of embodiment, they can be clipsed on said bars. They can be of any plastic material or other material. In the closed position, the handle (20¹) of the pin is directed downwardly, while the anchoring tongs (21) are closely adjusted on the vertical bars of the clevis, preventing thereby any oscillation within the horizontal plane of the latter, thanks to the plurality of the anchoring points. In the open position, the handle (20¹) is abutted on the finger (23), releasing thereby said bars from the anchoring tongs; it is possible then to determine the loaded weight of the measure. It is obvious that other interlocking means can be used. For instance, as illustrated FIG. 6, the brackets (18) are provided with openings (18²) for the engagement of the third pin (20), which is abutted either against a first finger (25) in the interlocked position of the clevis, or against a second finger (26) in the unlocked position.

Figure 9:
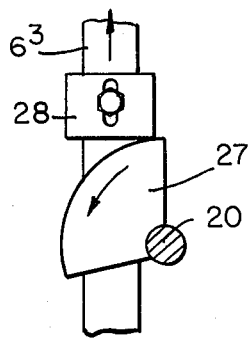
FIG. 9 is an alternative form of embodiment, on a larger scale, of the interlocking and unlocking means of the clevis for the support of the measure, said means being shown in the unlocking position.
Figure 10:
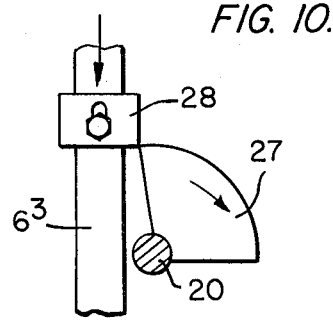
FIG. 10 is a view in accordance with FIG. 9, the means being shown in the interlocking position.
Figure 7:
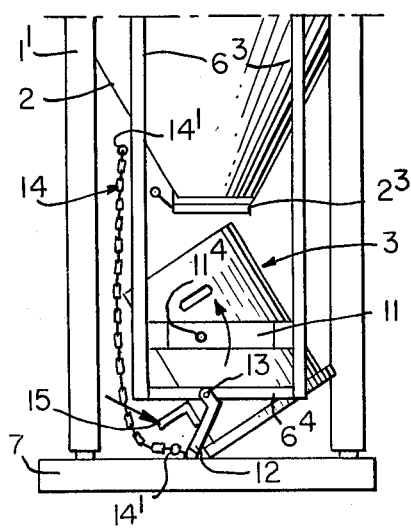
FIG. 7 is a view illustrating an operational step of the apparatus with the forward tilting of the measure to release the latter from the retaining element thereof, in accordance with the control of the operator.
Figure 8:
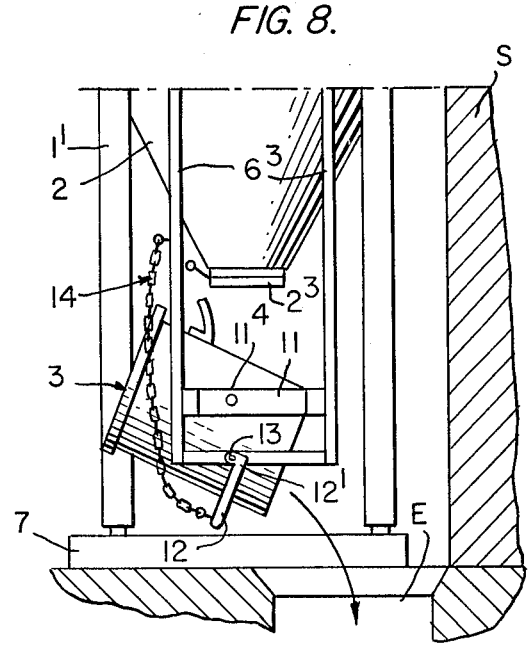
FIG. 8 is a view illustrating the next operational step of the apparatus, with the rearward tilting of the measure, for the discharge of the cereals once they are weighed out.

As illustrated FIG. 9 and 10, means are provided for interlocking the clevis (6) in position, while preventing on the one hand the oscillation thereof within the horizontal plane, and on the other hand the abutment of this clevis on the scale of the weighing machine during the filling and emptying steps. For this purpose, as illustrated, cams (27) are provided on the third pin (20) opposite each vertical bar of the clevis, said cams being secured by any convenient means such as welding.

In the position illustrated FIG. 9, the clevis is free in such a manner that the cams (27) will be away from said bars. For interlocking the bars, the handle (20¹) is actuated, causing the pin to be pivoted. The cams (27) are also pivoted and are gradually abutted on stops (28) which are inserted and fixed on each one of said bars. By their depressing action on the lower face of the stops, the cams cause the clevis to be lifted, eliminating thereby any weight on the weighing machine. For the adjustment in position of the stops on the bars, vents have been provided within which the fastening means are secured. With this arrangement, it is possible therefore to eliminate both the oscillation of the clevis within the horizontal plane, and the abutment thereof on the scale of the weighing machine, the warping of this scale being prevented thereby.

Deflectors (29) are also provided on each one of the horizontal cross-pieces of the clevis and of the frame, in order to discharge the cereals to the ground.

The operation of the apparatus will be now explained: As illustrated FIG. 1, the apparatus is positioned near a corn silo, for instance, (S) with a mouth (S1) for the incoming of the cereals into the tapering hopper. A discharge opening (E) is provided at the ground, with the apparatus engaged around this opening.

The first step takes place prior to filling the hopper; at this time, the measure-holding clevis is interlocked securely. Thereafter, the hopper is filled. Then the opening of the closure door allows the products to fall down into the measure. When the measure is full, the roll (17), without closing the closure door, serves to make flush the contents of the measure.

The next step consists in unlocking the clevis (6); the amount weighed is then read out while taking into account or not the allowance for the tare, in accordance with the presetting of the weighing machine. Thereafter, a further interlocking operation of the clevis takes place. The pedal (15) is then depressed by the operator by disengaging the lower portion thereof rearwardly, causing thus a slight forward tilting of the measure. The arch (12) for maintaining the measure in position is collapsed. Due to the shifting of the rotational axis of the measure and to the weight of the latter, the measure is tilted rearwardly in a reverse motion, permitting thus the cereals which have been weighed out to be discharged. The measure is lifted when it is empty, and then it is sufficient to grip the small chain and to lift the arch (12) which is abutted again against the measure, interlocking the latter in a position for a further operational sequence.

A development of the invention will be set forth now, with the use of the apparatus for taking away the granulous products, cereals or the like, directly when dropping them down from the discharge trap of a vehicle into the pit for receiving the products.

Figure 11:
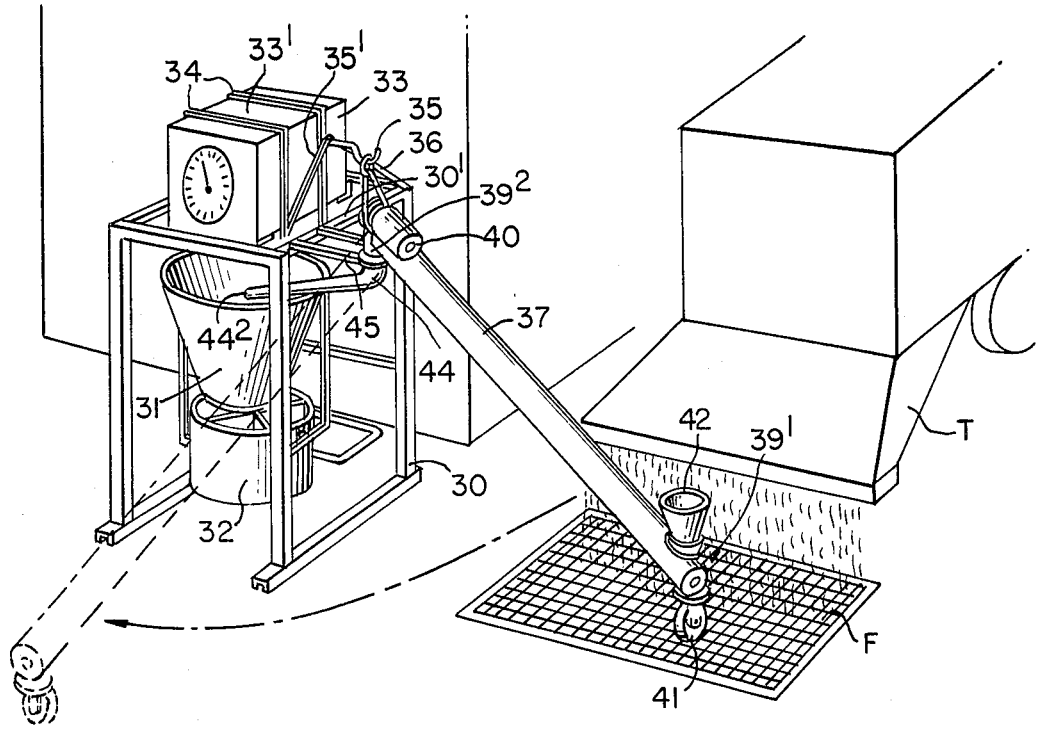
FIG. 11 is on a smaller scale a perspective view of the apparatus equipped with the feeder in accordance with the invention, the feeder being directed perpendicularly opposite the products being poured down from a vehicle in the receiving pit for a batch of products to be taken away. The retracted position of the feeder is illustrated by the dotted line.
Figure 12:
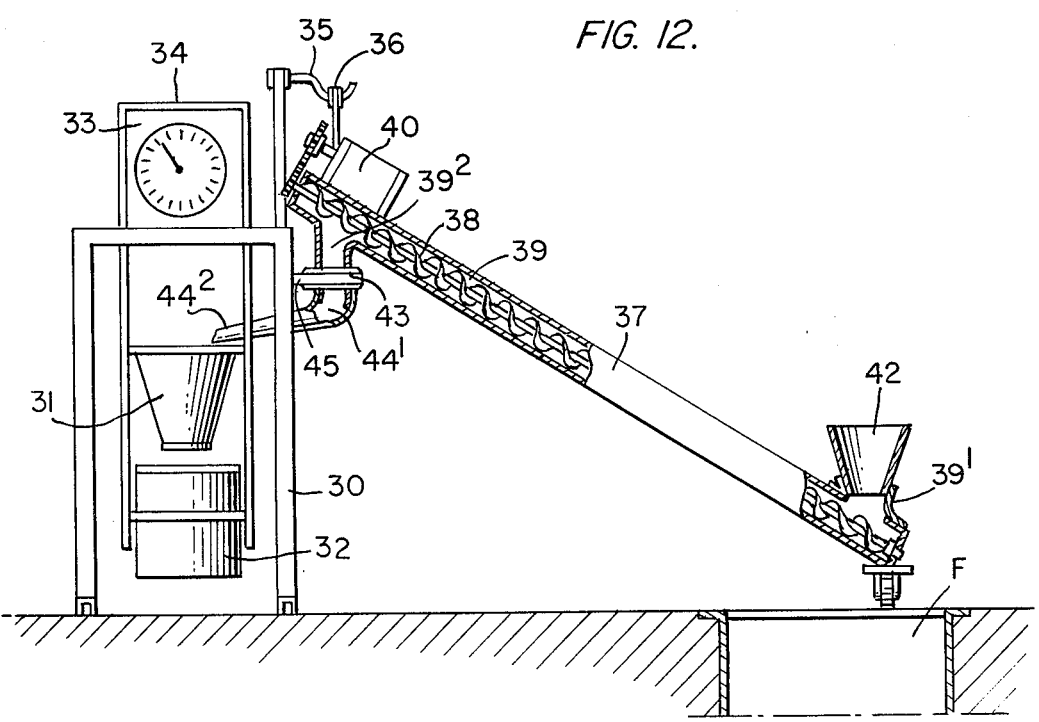
FIG. 12 is a cross-sectional side view corresponding to FIG. 11.

There will be seen in FIG. 11 an apparatus for determining automatically the mass by the hectoliter of various products, with a frame (30) within which are positioned independently a hopper (31) for the reception of the products and a measure (32) of reference; a weighing machine (33) being disposed in the upper portion of the frame (30) and receiving on the scale (33¹) thereof a clevis (34) supporting at the lower portion thereof said measure (32). Interlocking means for the clevis (34) are also provided, as well as the means for the tilting of said measure after the determination of the mass.

In accordance with a characteristic, one of the lateral or transverse upper cross-bars (30¹) connecting the posts of the frame (30) permits the vertical fastening of a small bridge (35¹) which is provided at the axial upper portion thereof with a protruding finger forming a hook (35). This hook co-operates with a suspension ring (36) which is made fast with the end of a known feeder (37) with worm screw (38) housed within a tubular body (39) and driven for rotation by a motor (40). This elevator resting at the opposite end on the ground through the intermediary of one or more castors or rollers (41) is thus pivoted, both horizontally and vertically, around the hook (35) so that it will be presented either in a transverse operational position, as illustrated in FIG. 11, or in a retracted lateral position, as shown by the dotted lines.

The lower portion of the body (39) of the feeder receives at right angles with the upper inlet opening (39¹) thereof for the arrival of the product an open receptacle (42) in the form of a funnel which is mounted hinged or not to be presented horizontally for any angular positioning of said feeder (37). The purpose of this receptacle (42) is to be presented within the path of the product falling down when it is dropped from the door-trap (T) of a vehicle into the receiving pit (F).

The opposite upper portion of the body (39) receives at right angles with the lower outlet opening (39²) thereof for the product having been conveyed a rigid or half-rigid sleeve (43) secured by driving in or otherwise so that said sleeve will be projecting downwardly and freely centered within the corresponding upper opening ($44^1$) of a hopper (44). The latter is secured transversely on the cross-bar ($30^1$) of the frame or possibly on one of the posts thereof, through the intermediary of a profiled support (45) which forms a collar, and this hopper forms at the bottom thereof a taper-shaped bent chute ($44^2$) the discharge orifice of which is presented opposite the axial portion of the upper opening of the hopper (31) incorporated by the apparatus.

It will be obvious that in accordance with these arrangements, the feeder as described may be of any other type, more particularly of the flexible type, while being capable in any case to operate inversely for the discharge through the open orifice ($39^1$) of the lower portion thereof, into the receiving pit (F), of the products contained within the body (39) of the feeder, for the sole purpose to prevent any mixing when products of various nature are taken away in succession.

When the products are dropped down into the receiving pit (F) owing to the opening of the trap-door (T) of the vehicle carrying the product, the feeder (37) is moved manually by means of the castor (41) thereof in order to be pivoted around the hook (35), so that the feeder will be presented perpendicularly and transversely as illustrated in FIG. 11, while taking also into account the unevenness of the ground and of the gradient in the vertical positioning of the apparatus.

The open receptacle (42) is placed horizontally opposite the products dropping down, in order to permit the products to be taken away and carried away by the operation of the motor (40). The products are thus poured down through the sleeve (43) within the opening ($44^1$) and are guided therefrom through the chute ($44^2$) directly into the hopper (31) of the apparatus, for the filling thereof after interlocking the measure-holding clevis. Afterwards, the operational steps of the apparatus remain the same as the ones which have been described previously.

When the products, once weighed out, have been taken away and discharged, directly or indirectly, into the receiving pit (F), by shovelling or otherwise, the motor (40) of the feeder is switched over in reverse operation to permit the discharge of the non-distributed products located within the turns of the driving worm screw (38) and outside the apparatus.

After use, the feeder (37) is pivoted to be retracted laterally relative to the apparatus, as illustrated in dotted lines in FIG. 11.

The apparatus can be entirely automatized by any suitable control means, either hydraulic, pneumatic or electric means. The automatisms can be considered at the level of the relationship between each one of the means within the operational relationship thereof with the other means. It is also possible to provide a device for the remote reading of the mass by the hectoliter, as well as an electric or electronic programming, to permit for instance the shifting of the feeder; the latter may also be controlled for translation by a gearing device conveniently positioned.

We claim:

1. A device which permits the determination of specific weight of various materials comprising:
    a frame;
    a tapering hopper within said frame;
    a measure within said frame; and
    a weighing machine within said frame assembled such that said hopper and said reference measure are independently positioned within said frame, such that said weighing machine is located in the upper part of said frame, and such that said weighing machine additionally comprises:
    a scale;
    a clevis which supports said measure; and means for locking said clevis while filling, leveling and emptying of said hopper and for unlocking said clevis while weighing, such that said means permits the tipping of the measure after determination of specific weight.

2. A device as in claim 1 where said hopper is supported by two arches which are curved in order to cooperate with the edge of said hopper and where said hopper has a closure door on its bottom.

3. Device according to claim 1, characterized in that it comprises a mechanical feeder driven by a motor fixed in articulated suspension and offset at the upper part of the frame and provided at its base with means for rolling on the floor solely for permitting it to be oriented by pivoting to perpendicularly present its admission orifice opposite the falling products when they are poured from the transporting vehicle into the receiving pit, that the upper discharge orifice of the feeder cooperates with a hopper for an automatic pouring of the products into the hopper inherent in the device in order to obtain in this manner a check sampling.

4. Device according to claim 3, characterized in that the feeder, with a rigid or flexible body, receives an open receptacle in the form of a funnel at its base to the right of its upper admission opening for the products, which receptacle is permanently fixed or mounted with the possibility of an angular movement in relation to the longitudinal axis of the feeder so as to present its axis in the path of the falling products.

5. A device as in claim 1, such that said means for locking or unlocking said clevis comprises profiled brackets attached to the vertical bars of said frame and a bracing cross-bar located between the back pair of said vertical bars of said frame located at the same level as said brackets, said profiled brackets being arranged so that they can receive a freely rotating third pin which extends at its front end in the form of a gripping handle in its end positions.

6. A device according to claim 5 such that said locking means are U-shaped sections in the form of interlocking elements which enclose the vertical bars of the clevis whereby said clevis is kept from oscillating in a horizontal plane.

7. A device as in claim 5 such that said locking means are cams which cooperate during the pivoting of said third pin with strips put in a regulatable position on the clevis in such a manner as to avoid any oscillation in a horizontal plane and to bring about the raising of said clevis in relation to said scale.

8. A device as in claim 1 where the upper part of said clevis is supported and centered on said scale of said weighing machine, where said clevis extends downward in the form of vertical bars to which are fixed at different levels support means for said measure, support means for a flushing roll and means which permit the tipping of said measure after determination of the weight.

9. A device as in claim 8 such that two profiled lugs are provided on said vertical bars of said clevis carrying said measure at the level of the top of said measure, said lugs permitting the positioning of a flushing roll, such that one of said lugs located on a back bar of said clevis engages a second finger on said flushing roll and such that said flushing roll is supported on said two lugs while in non-use.

10. A device as in claim 8 where profiled plates are connected and fixed at each of their ends to said vertical bars of said clevis, where each said plate has an off-set central portion provided with opening which permits the engagement and support of two pins connected and fixed to said measure such that said pins are free to rotate in said openings and where said measure has hand grips attached to it.

11. A device as in claim 10 such that said pins are off-set in relation to the median transversal axis of said measure.

12. A device as in claim 11 such that a third arch which can be retracted by an operator is supported by its central part against the lower part of said measure, while the ends of said third arch are arranged so that they are basically supported along the lower cross-pieces of said clevis and engage a finger integral with said lower cross-pieces in a freely pivoting manner.

13. A device as in claim 12 such that a small chain connects by its ends said third arch and one of said vertical bars of said clevis with a looseness corresponding to a maximum lowering of said third arch in relation to its initial position.

14. A device as in claim 12 such that a pedal is located slightly above the support plane of said third arch on said measure.

* * * * *